United States Patent
Preciutti

[11] Patent Number: 5,127,415
[45] Date of Patent: Jul. 7, 1992

[54] MULTI-PURPOSE DENTAL APPLICATOR

[76] Inventor: Roberto Preciutti, 5883 Cape Horn Dr., Agoura Hills, Calif. 91301

[21] Appl. No.: 690,533

[22] Filed: Apr. 23, 1991

Related U.S. Application Data

[63] Continuation-in-part of Ser. No. 509,287, Apr. 13, 1990, Pat. No. 5,010,906.

[51] Int. Cl.$^5$ .............................................. A61C 15/00
[52] U.S. Cl. .................................. 132/323; 132/308; 433/147; 128/62 A; 15/167.1
[58] Field of Search .............. 132/308, 309, 310, 311, 132/322, 323, 324, 325, 326, 327; 433/127, 128, 129, 146, 147; 128/62 A; 15/167.1, 167.2

[56] References Cited

U.S. PATENT DOCUMENTS

| | | | |
|---|---|---|---|
| 1,346,125 | 7/1920 | Hasbrook | 132/324 |
| 1,480,101 | 5/1924 | Ogden | 132/324 |
| 2,187,899 | 12/1938 | Henne | 132/323 |
| 2,507,587 | 5/1950 | Bjorklund | 433/129 |
| 2,837,098 | 6/1958 | Sorboro | 132/324 |
| 3,631,869 | 10/1977 | Espinosa | 132/323 |
| 3,847,168 | 1/1974 | Schlegel | 132/309 |
| 3,851,984 | 12/1974 | Crippa | 433/127 |
| 3,924,334 | 12/1975 | Lentine et al. | 433/147 |
| 3,927,686 | 11/1975 | Zambito | 132/323 |
| 3,991,776 | 11/1976 | Duffy | 132/311 |
| 4,114,276 | 9/1978 | Malata et al. | 433/129 |
| 4,235,253 | 11/1980 | Moore | 132/322 |
| 4,319,595 | 3/1982 | Ulrich | 132/309 |
| 4,796,325 | 1/1989 | Bortman | 15/167.2 |
| 4,880,382 | 11/1989 | Moref et al. | 132/309 |
| 4,920,992 | 5/1990 | Preciutti | 132/323 |
| 5,010,906 | 4/1991 | Preciutti | 132/323 |

FOREIGN PATENT DOCUMENTS 943610 12/1963 United Kingdom ............... 433/129

Primary Examiner—Gene Mancene
Assistant Examiner—Frank A. LaViola
Attorney, Agent, or Firm—Thomas I. Rozsa

[57] ABSTRACT

A multi-purpose dental applicator including a handle and an interchangeable removable member which can be a yoke supporting a length of dental floss, a toothbrush, a spiral wound wire tooth cleaning brush, a rubber tip gum massager, or a length of abrasive tape. The handle has an elongated stem for gripping purposes and a head piece having a receiving cavity for receiving the stem of the interchangeable removable member. The handle further incorporates threads on the outer surface of the head surrounding the receiving cavity. In the preferred embodiment, the receiving cavity is an opening extending into the body of the head in a generally inverted frustum shaped configuration which then extends into a spherical shaped cavity and thereafter extends into an arcuate section having the circumferential length of approximately twenty degrees to either side of the vertical or longitudinal axis of the head. This cavity is designed to receive a specially designed stem which design is common to all of the interchangeable removable members. The handle further comprises a slidable and threaded collar which can be slid onto and screwed around the opening to tighten the interchangeable removable member to the handle.

28 Claims, 4 Drawing Sheets

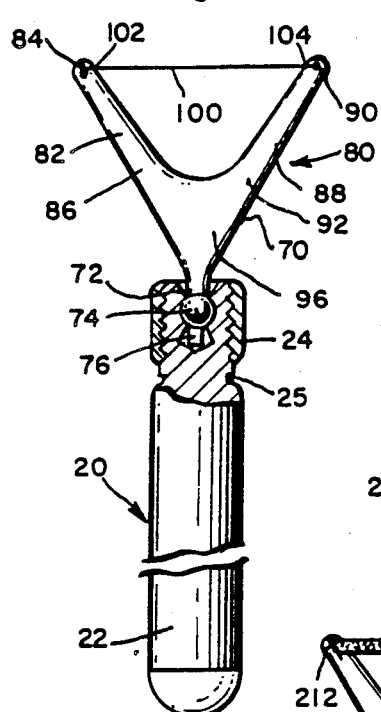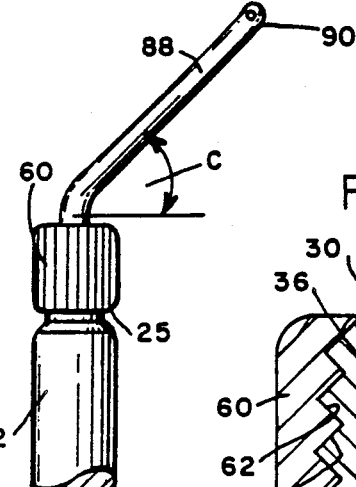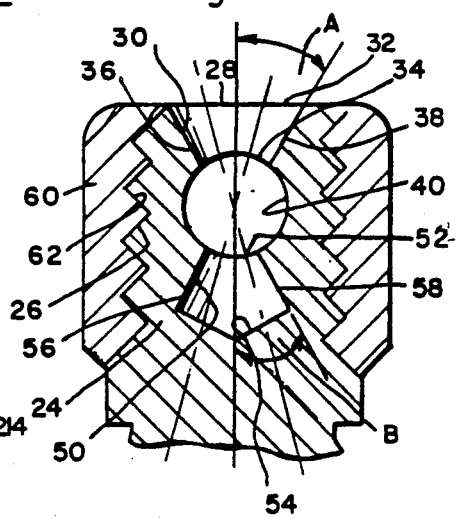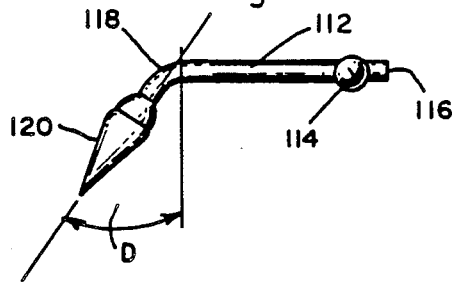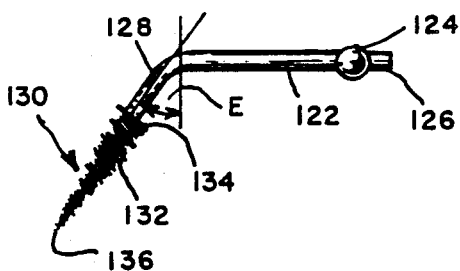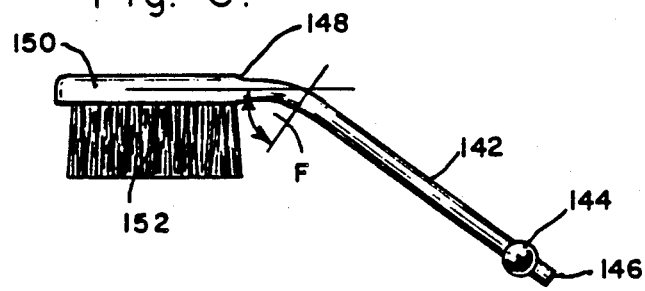

MULTI-PURPOSE DENTAL APPLICATOR

This patent application is a Continuation-In-Part of the Co-pending patent application Ser. No. 07/509,287 filed on Apr. 23, 1990, now U.S. Pat. No. 5,010,906.

BACKGROUND OF THE INVENTION

The present invention relates to the field of dental apparatus used by the consumer such as dental floss, toothbrushes, spiral wire tooth cleaning brushes, and dental massaging rubber tips. More particularly, the present invention relates to the field of dental flossing apparatus which are designed to hold a length of dental floss in a given manner such that it can be used to clean the interstices between adjacent teeth. The present invention also relates to an interchangeable multi-purpose applicator which can retain a dental floss apparatus, a toothbrush, a wire tooth cleaning brush, and a rubber gum massager.

2. Description of the Prior Art

The inventor is also the inventor of U.S. Pat. No. 4,920,992 issued on May 1, 1990 for "Dental Flossing Apparatus". Through prosecution of that patent, the inventor has become aware of the following prior art. In most conventional practice, an individual using dental floss to clean the interstices between the user's teeth unwraps a length of dental floss from its container and wraps one end of the floss around a finger of one hand and wraps the opposite end of the floss around a finger of the other hand and thereafter holds the length of floss taut between the two fingers so that it can be inserted between two adjacent teeth and moved back and forth to clean the area. One problem with this method is that a large amount of floss is used. Second, it is sometimes difficult to reach back areas of the mouth when holding the length of floss in this manner.

In some instances, attempts have been made to provide devices for holding the length of floss, which usually takes the form of a yoke across which a portion of the floss is trained while the opposite ends are wrapped about the projecting legs of the yoke. The entire apparatus is then placed in the user's mouth while the fingers manipulate the device between the teeth for cleaning. Several prior art patents disclose variations on this concept. They are as follows:

1. U.S. Pat. No. 3,927,686 issued in 1975 to Zambito for "Dental Floss Holder".
2. U.S. Pat. No. 3,631,869 issued in 1972 to Espinosa for "Dental Floss Holder".
3. U.S. Pat. No. 3,847,168 issued in 1974 to Schlegel for "Tooth Cleaning Appliance".
4. U.S. Pat. No. 2,837,098 issued in 1958 to Sorboro for "Dental Floss Holder And Dispenser".
5. U.S. Pat. No. 1,480,101 issued in 1924 to Ogden for "Dental Floss Appliance".
6. U.S. Pat. No. 2,187,899 issued in 1940 to Henne for "Dental Floss Throw-Away Unit".
7. U.S. Pat. No. 1,346,125 issued in 1920 to Hasbrook for "Sanitary Teeth Cleaner".
8. U.S. Pat. No. 4,319,595 issued in 1982 to Ulrich for "Dental Care Unit".

The apparatus disclosed in Zambito has several disadvantages. Besides being expensive to manufacture, the method of attaching the head holding the floss to the handle cannot provide a firm and secure grip on the head. As a result, when used with vigorous action as is common when flossing, it is possible for the head to come loose and fall into the user's throat and cause the user to choke. In addition, the device does not provide a universal choice of positioning the head orientation and therefore certain parts of the mouth such as the back teeth may be difficult to reach and clean with this device. Further, Zambito does not provide a choice of flossing means and it is also vitally important to prevent sagging of the floss itself.

The apparatus disclosed in Espinosa also has several problems. Not enough tension can possibly be applied to the floss by this method. During flossing, the floss would sag and make the floss device useless. As with the device in Zambito, the device does not provide a universal choice of positioning the head orientation and therefore certain parts of the mouth such as the back teeth may be difficult to reach and clean with this device. In addition, this device with its many grooves, channels, indentations and other slot attachments is an expensive device to manufacture.

The apparatus disclosed in Schlegel is also an expensive and cumbersome device to manufacture and further has a complicated way for retaining the floss. The floss can easily become loose and sag making it worthless for flossing. In addition, the yoke has only one orientation, making it difficult to reach certain parts of the mouth.

The apparatus disclosed in Sorboro, Ogden, Henne, and Hasbrook also have many of the disadvantages previously discussed The yoke holding the floss is once again in a fixed orientation making it difficult to reach certain parts of the mouth. The complicated structure is also expensive to manufacture.

The apparatus in Ulrich is a dental water pick.

Overall, the prior art embodiments of yoke apparatus which retain a length of dental floss all have in common one or more of the following defects. First, the yoke is oriented in a fixed position and cannot be adjusted to accommodate difficult locations in the mouth. Second, the device is complicated and expensive to manufacture. Third, the floss itself is not held securely and can easily sag and come loose during use, thereby making it worthless. Therefore, there is a significant need for a flossing apparatus which overcomes these defects.

There is no device known to the inventor which operates as a multipurpose apparatus to interchangeably support a dental floss device, a toothbrush, a spiral wound wire tooth cleaning brush and a rubber tip gum massager.

SUMMARY OF THE PRESENT INVENTION

The present invention relates to an improved multipurpose dental applicator comprising a handle and an interchangeable removable member which can be a yoke supporting a length of dental floss, a toothbrush, a spiral wound wire tooth cleaning brush, or a rubber tip gum massager The handle comprises an elongated shank for gripping purposes and a head piece having a receiving means for receiving the shank of the interchangeable removable member. The handle further comprises threads on the outer surface of the head surrounding the receiving means. In the preferred embodiment, the receiving means is an opening extending into the body of the head in a generally inverted spherical shaped cavity and thereafter extends into an arcuate section having the circumferential length of approximately twenty degrees to either side of the vertical or longitudinal axis of the head. This cavity is designed to receive a specially designed shank which design is common to all of the interchangeable removable members. The handle further comprises a slidable and threaded collar which can be slid onto and screwed around the opening to tighten the interchangeable removable member to the handle.

The interchangeable removable member has a similar section and a modified section for each of the members. The similar section comprises an elongated shank by which the member is held in the handle. The elongated shank has proximate one end a spherical ball and an elongated stem section extending from the ball in alignment with the shank. Proximate its opposite end, the shank extends into the specific interchangeable part. In one embodiment, the part is a yoke comprising two arms for retaining a length of dental floss between them. In the preferred embodiment, the arms of the yoke are aligned at approximately thirty-five degrees to the stem section. In a second embodiment, the part is a rubber tip for massaging gums and comprises a central core shank with the rubber tip mounted on it. In the preferred embodiment, the central core shank and rubber tip are aligned at approximately thirty-five degrees to the stem section. In a third embodiment, the part is a spiral wound wire tooth cleaner comprising a central core shank and wire bristles spirally wound around the shank. In the preferred embodiment, the central core shank is aligned at approximately thirty-five degrees to the stem section. In a fourth embodiment, the part is a toothbrush. In the preferred embodiment, the head of the toothbrush is aligned at approximately thirty-five degrees to the stem section while the bristles extend perpendicularly to the head. With each of the four pieces, the shank terminating in a sphere with a stem extending from the sphere and aligned with the shank provides a stable means for supporting the interchangeable removable member within the head of the handle. Once the shank is placed inside the cavity in the head of the handle, the sphere can be rotated in the horizontal plane within the spherical cavity and the stem can be rocked forward and backward or from side to side within the twenty-degree arc of the cavities above and below the spherical cavity. With the preferred embodiment having the operating part set at approximately thirty-five degrees to the stem, the angle of the part relative to the handle member can be rotated from fifty-five degrees to fifteen degrees relative to the handle. Once the piece is rotated to the desire angle relative to the handle, the collar can be slid onto the threads on the outer surface of the head of the handle and threaded into place so that the shank, sphere and stem of the interchangeable removable piece can be retained securely within the handle so that it cannot possibly fall out and fall into a user's throat during use and at the same time can be oriented at the desired angle to accommodate different locations in the user's mouth.

It has been discovered, according to the present invention, that if an interchangeable removable section comprises a shank having a spherical tip and a stem extending from the spherical tip and aligned with the shank, then the interchangeable removable section can be inserted into a receiving cavity in the head of a handle and oriented at any desired orientation relative to the handle so that any desired location of the mouth can be reached by the operating portion of the interchangeable removable section.

It has further been discovered, according to the present invention, that if the handle comprises a spherical cavity with a pair of arcuate cavities located above and below the spherical cavity with the upper cavity shaped as a frustum and the lower cavity generally arcuate with both cavities having a spread of twenty-degrees relative to the vertical or longitudinal axis of the head, then the shank section of the removable interchangeable member can be inserted into the cavities such that the sphere on the shank can fit within the spherical cavity, the stem portion fits into the lower arcuate cavity and a portion of the stem rests within the upper frustum shaped cavity such that the stem can be rotated in the horizontal plain at any 360 degree orientation while the stem can also be moved to the limited arcuate distance relative to the head.

It has additionally been discovered that if the handle further comprises a slidable collar which contains securing means for tightening the shank and its sphere and stem onto the collar, then the shank can be securely tightened onto the head to prevent it for coming loose during use.

It has also been discovered, according to the present invention, that any dental device can be incorporated onto the shank of the removable interchangeable member such as a yoke containing a length of dental floss between the yoke members, a toothbrush, a spiral wire tooth cleaning brush, a rubber tip gum massager, and a yoke containing a length of abrasive tape between the yoke members.

It has additionally been discovered that if a container comprises an accommodating opening to receive a multiplicity of the interchangeable members, then the members can be kept in a sanitary condition. For example, in one embodiment, a multiplicity a yokes having a length of dental floss can be retained and subsequently discarded after use. Similarly, yokes having a length of abrasive tape can be retained and subsequently discarded after use. Other more expensive items such as the toothbrush, spiral wound wire brush and rubber tip gum massager can be retained in a sanitary manner and cleaned before being replaced in the container.

It has further been discovered, according to the present invention, that if the handle of the dental applicator device has a slit with inner recesses, and the interchangeable removable members each have a stem with outer protrusions, then the interchangeable removable members can be secured onto the handle by having the stem of the interchangeable removable member inserted into the slit of the handle, such that the protrusions of the stem are engaged into the recesses of the slit.

It is therefore an object of the present invention to provide a dental applicator device having a handle which can accommodate various interchangeable removable devices which each can be oriented in any desire orientation relative to the handle so that the operating portion of interchangeable removable member which may be dental floss, a toothbrush, a spiral wound wire brush, a rubber tip gum massager, or abrasive tape can reach any desired portion of the mouth.

It is also an object of the present invention to provide a dental device wherein each of the interchangeable removable members can be securely retained on the handle during use so that the removable interchangeable member cannot come loose during use and accidentally fall into the user's throat.

It is an additional object of the present invention to provide a retaining means for retaining a multiplicity of each of the interchangeable removable members in a sanitary manner so that they can be used and either discarded or else washed and replaced for subsequent use.

It is an additional object of the present invention to provide a dental applicator device having a handle which has a slit with inner recesses, and a multiplicity of interchangeable removable members each have a stem with outer protrusions, so that each interchangeable removable member can be secured onto the handle by having the stem of the interchangeable removable member inserted into the slit of the handle, such that the protrusions of the stem are engaged into the recesses of the slit.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a front elevational view of the present invention dental applicator shown in partial cross-section with an interchangeable member being a yoke supporting a length of dental floss between the arms of the yoke supported in the handle.

FIG. 2 is a side elevational view of the present invention dental applicator with an interchangeable member being a yoke supporting a length of dental floss between the arms of the yoke supported in the handle.

FIG. 3 is an enlarged cross-sectional view of the head and collar illustrating the specialized cavity within the head of the handle.

FIG. 4 is side elevational view of a second interchangeable member which is a rubber tip gum massager.

FIG. 5 is side elevational view of a third interchangeable member which is a spiral wound wire brush tooth cleaner.

FIG. 6 is side elevational view of a fourth interchangeable member which is a toothbrush.

FIG. 11 is side elevational view of a fifth interchangeable member which is a yoke supporting a length of abrasive tape between the arms of the yoke.

DETAILED DESCRIPTION OF THE PREFERRED EMBODIMENT

Figure 7:
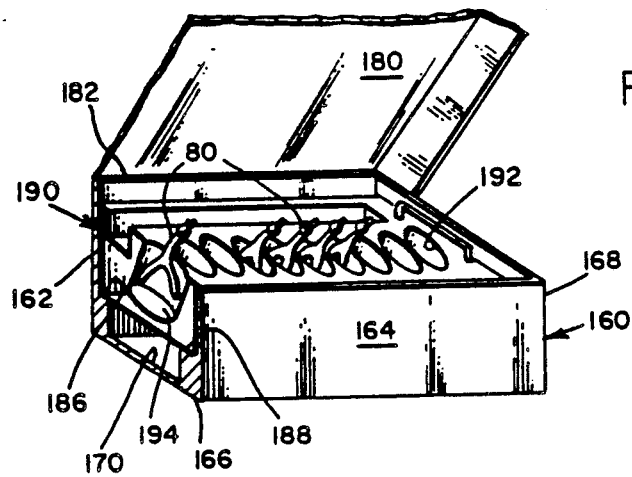
FIG. 7 is a perspective view in partial cross-section of a container for retaining a multiplicity of the first interchangeable removable members, each of which is a yoke supporting a length of dental floss between the arms of the yoke.

Although specific embodiments of the invention will now be described with reference to the drawings, it should be understood that such embodiments are by way of example only and merely illustrative of but a small number of the many possible specific embodiments which can represent applications of the principles of the invention. Various changes and modifications obvious to one skilled in the art to which the invention pertains are deemed to be within the spirit, scope and contemplation of the invention as further defined in the appended claims.

Referring particularly to FIGS. 1 and 3, there is shown at 20 the specific handle of the present invention multi-purpose dental applicator. The handle 20 comprises an elongated shank section 22 and a head section 24. While the shank section is shown as cylindrical, it will be appreciated that any other design such as rectangular can also be used with the present invention. While the surface of the shank is shown as smooth, it can also include ribs for more easy gripping. The head section 24 further comprises threads 26 on its exterior surface. The upper portion of the head section 24 also comprises an internal opening 28 leading to three internal cavities. The first cavity 30 is generally in the shape of a frustum, having base opening 32 which is aligned with opening 28 in the top of the head 24 and internal surface 34. Slanted walls 36 and 38 are aligned so that there is an angle "A" between the walls and the longitudinal axis of the head 24. In the preferred embodiment, the angle "A" is approximately 20 degrees. First cavity 30 extends into second cavity 40 which is spherical. The circumference of second spherical cavity 40 is aligned with internal surface 34 of first cavity 30. Beneath spherical cavity 40 is third arcuate cavity 50 having upper surface 52 also aligned with the circumference of spherical cavity 40. The lower extremity of arcuate cavity 50 is bounded by arcuate surface 54. Slanted walls 56 and 58 are aligned so that there is an angle "B" between the walls and the longitudinal axis of the head 24. In the preferred embodiment, the angle "B" is three cavities 30, 40 and 50 are contiguous. The head section further comprises a collar 60 having internal threads 62. The collar can be rotated down from the head 24 and extended onto the neck section between shank section 22 and head section 24. In this way, the head section 24 is loosened and can accept the shank of the associated interchangeable removable member.

The present invention is primarily used with five different interchangeable removable members. One such member which is the dental flossing yoke is illustrated in place in FIGS. 1 and 2. The interchangeable removable yoke member 70 comprises an elongated shank 72 which extends into a spherical ball 74 at its lowermost tip. Extending from the spherical ball at a location diametrically opposite to the attachment point of the shank 72 is a stem 76 which is aligned with the shank 72. The assembly is designed to be accommodated within the three cavities such that the spherical ball 74 pops into the spherical cavity 40 and is rotatably retained therein. The stem 76 fits within lowermost arcuate cavity 50 while a portion of the shank 72 rests within upper frustum shaped cavity 30. Once in place, the threaded collar 60 is rotated from the neck 25 onto the threads 26 of head section 24 so that it creates a tight fit of the assembly of shank 72, spherical ball 74 and stem 76 within the head 24. In this way, the assembly is held securely within the head 24.

The opposite end of the shank 72 remote from the spherical ball 74 then extends to the operating device. The first operating device is a dental floss retaining yoke 80. The yoke 80 comprises a pair of arms 82 and 88. Arm 82 is set at a vertical angle and terminates in a rounded tip 84 at its upper end. The lower end 86 of arm 82 is formed into yoke base 96. Arm 88 is set at a vertical angle and terminates in a rounded tip 90 at its upper end. The lower end 92 of arm 88 is formed into yoke base 96. The two arms 82 and 88 extend away from each other to form a generally "V" shaped configuration. The yoke base 96 extends into shank 72. The arms 82 and 88 are aligned in the same vertical plane. As illustrated in FIG. 2, in the preferred embodiment the arms 82 and 88 and yoke 80 are aligned at an angle "C" relative to shank 72. In the preferred embodiment, the angle C is approximately 35 degrees Stretched across the interior upper area of the yoke 80 adjacent rounded tips 84 and 90 is a piece of dental floss 100. End 102 of dental floss 100 is bonded to the rounded tip 84 of arm 82. End 104 of dental floss 100 is bonded to the rounded tip 90 of arm 88. The bonding means may be glue or other suitable adhesive which serves to bond the dental floss 100 to the tips of the arms of the yoke 80. Alternatively, the process can be provided wherein the length of dental floss 100 is directly bonded to the tips as the yoke 80 is being molded. In this way, the dental floss 100 is held taut between the tips of the arms of the yoke and therefore cannot come loose and will not sag during use. Therefore, with the shank 72, spherical ball 74 and stem 76 inserted as previously described, the yoke 80 can be oriented in any horizontal plane (plane perpendicular to the longitudinal axis of the head 24 and shank 22) and also rotated relative the head 24 within the limits of cavities 30 and 50 until the desired orientation of the yoke 80 relative to the handle 20 is achieved. With angles A and B each being 20 degrees and angle C being 35 degrees, it will be appreciated that the orientation of the yoke 80 relative to the handle 20 will range between 15 degrees and 55 degrees. After the proper orientation is achieved, the collar 60 is tightened onto the head 24 as previously described and the apparatus is set for use.

After use, the collar is loosened by being threaded off the head 24 so that it rests on neck 25 and the yoke apparatus 80 is removed.

Similarly, the remaining interchangeable removable members can be inserted and used. Referring to FIG. 4, the second interchangeable removable member is a rubber tip gum massager. The same three components are now numbered 112 for the shank, 114 for the spherical ball and 116 for the stem. The shank 112 at its location opposite from the spherical ball 114 extends into a shank 118 which in turn supports at its remote end a rubber tip gum massager 120 of conventional design. The shank 118 is preferably offset at an angle "D" relative to shank 112. In the preferred embodiment, the angle D is approximately 35 degrees. Therefore, with the shank 112, spherical ball 114 and stem 116 inserted as previously described, the rubber tip gum massager 120 can be oriented in any horizontal plane (plane perpendicular to the longitudinal axis of the head 24 and shank 22) and also rotated relative to the head 24 within the limits of cavities 30 and 50 until the desired orientation of the rubber tip gum massager 120 relative to the handle 20 is achieved. With angles A and B each being 20 degrees and angle D being 35 degrees, it will be appreciated that the orientation of the rubber tip gum massager 120 relative to the handle 20 will range between 15 degrees and 55 degrees. After the proper orientation is achieved, the collar 60 is tightened onto the head 24 as previously described and the apparatus is set for use. After use, the collar is loosened by being threaded off the head 24 so that it rests on neck 25 and the rubber tip gum massager apparatus is removed.

Referring to FIG. 5, the third interchangeable removable member is a spiral wound wire tooth cleaning brush. The same three components are now numbered 122 for the shank, 124 for the spherical ball and 126 for the stem. The shank 122 at its location opposite from the spherical ball 124 extends into a shank 128 which in turn supports along its length a spiral wound tooth cleaning brush 130. The brush 130 comprises a wire 132 which is wound in a spiral having a broader base 134 and terminating in a pointed tip 136. The shank 128 is preferably offset at an angle "E" relative to shank 122. In the preferred embodiment, the angle E is approximately 35 degrees. Therefore, with the shank 122, spherical ball 124 and stem 126 inserted as previously described, spiral wound wire tooth cleaning brush 130 can be oriented in any horizontal plane (plane perpendicular to the longitudinal axis of the head 24 and shank 22) and also rotated relative to the head 24 within the limits of cavities 30 and 50 until the desired orientation of the spiral wound wire tooth cleaning brush 130 relative to the handle 20 is achieved. With angles A and B each being 20 degrees and angle E being 35 degrees, it will be appreciated that the orientation of the spiral wound wire tooth cleaning brush 130 relative to the handle 20 will range between 15 degrees and 55 degrees. After the proper orientation is achieved, the collar 60 is tightened onto the head 24 as previously described and the apparatus is set for use. After use, the collar is loosened by being threaded off the head 24 so that it rests on neck 25 and the spiral wound wire tooth cleaning brush apparatus is removed.

Referring to FIG. 6, the fourth interchangeable removable member is a toothbrush. The same three components are now numbered 142 for the shank, 144 for the spherical ball and 146 for the stem. The shank 142 at its location opposite from the spherical ball 144 extends into a shank 148 which in turn extends into the head 150 of the toothbrush. Bristles 152 extend generally perpendicular to head 150. The shank 148 is preferably offset at an angle "F" relative to shank 142. In the preferred embodiment, the angle F is approximately 35 degrees. Therefore, with the shank 142, spherical ball 144 and stem 146 inserted as previously described, toothbrush head 150 can be oriented in any horizontal plane (plane perpendicular to the longitudinal axis of the head 24 and shank 22) and also rotated relative to the head 24 within the limits of cavities 30 and 50 until the desired orientation of the toothbrush head 150 and bristles 152 relative to the handle 20 is achieved. With angles A and B each being 20 degrees and angle F being 35 degrees, it will be appreciated that the orientation of the toothbrush head 150 relative to the handle 20 will range between 15 degrees and 55 degrees. After the proper orientation is achieved, the collar 60 is tightened onto the head 24 as previously described and the apparatus is set for use. After use, the collar is loosened by being threaded off the head 24 so that it rests on neck 25 and the toothbrush apparatus is removed.

Referring to FIG. 11, the fifth interchangeable removable member is another yoke, comparable to the device illustrated in FIGS. 1 through 3, but containing a length of abrasive tape 200 having abrasive material 210 thereon between yoke arms 82 and 88. The length of abrasive tape 200 may be affixed to the tips of the yoke arms through slots 212 and 214 in arms 82 and 88 respectively. Other conventional means may also be used to support the abrasive tape on the yoke arms. The abrasive tape can be used to scrape off stains such as coffee and tea stains between adjacent teeth. The tape 200 may also function as a tooth polishing tape.

Figure 10:
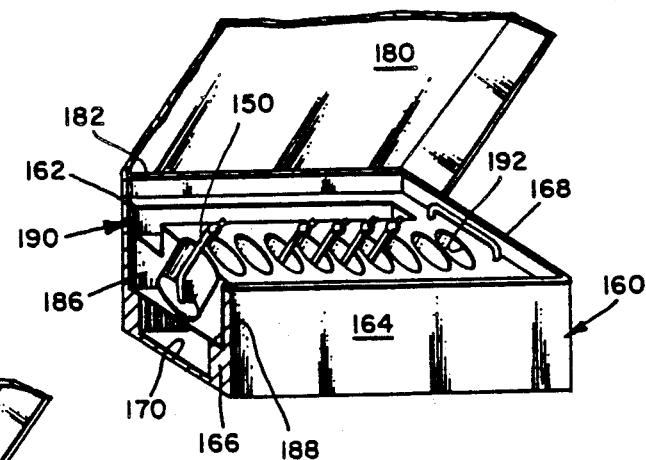
FIG. 10 is a perspective view in partial cross-section of a container for retaining a multiplicity of the fourth interchangeable removable member, each of which is a toothbrush.
Figure 9:
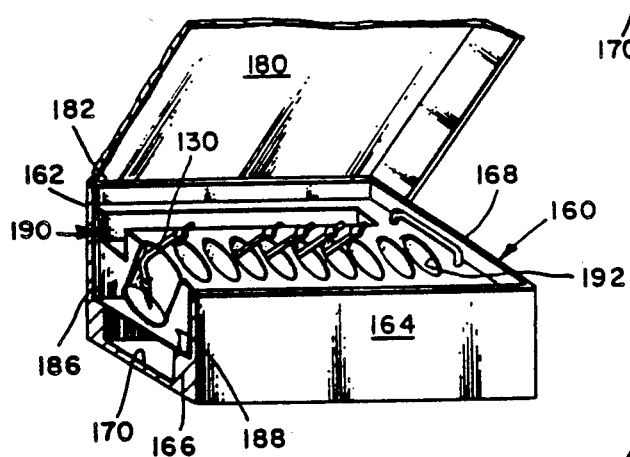
FIG. 9 is a perspective view in partial cross-section of a container for retaining a multiplicity of the third interchangeable removable member, each of which is a spiral wound wire brush tooth cleaner.
Figure 8:
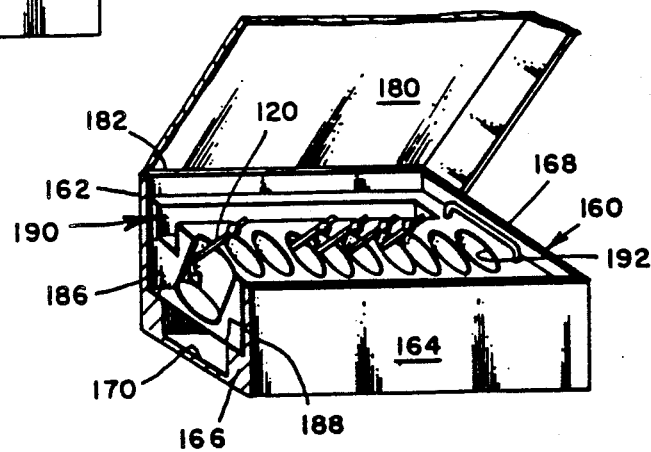
FIG. 8 is a perspective view in partial cross-section of a container for retaining a multiplicity of the second interchangeable removable member, each of which is a rubber tip gum massager.

A simple case apparatus can be used for retaining a multiplicity of a selected one of the interchangeable removable members. The case 160 is illustrated in FIGS. 7 through 10 and comprises a pair of parallel oppositely disposed longitudinal walls 162 and 164 and a pair of parallel oppositely disposed lateral walls 166 and 168, a bottom 170 and a top 180 which is hingably supported at one end 182 on longitudinal wall 162 so that it can be rotated to an opened position for access to the case. Longitudinal wall 162 further comprises an interior elongated shelf 186 offset by a distance from bottom 170. Longitudinal wall 164 further comprises an interior elongated shelf 188 offset by a distance from bottom 170. Removably retained on shelves 186 and 188 is a removable and interchangeable apparatus retaining member 190. The apparatus retaining member has a multiplicity of openings designed to conform to the shape of the specific interchangeable removable member being retained therein. In the case of the flossing yoke 80 or abrasive tape yoke apparatus retaining member 190, the openings 192 are generally oval as illustrated in FIG. 7. The oval configuration can also be used to accommodate the rubber tip gum massager as illustrated in FIG. 8, the spiral wound wire tooth cleaning brush as illustrated in FIG. 9 and the toothbrush as illustrated in FIG. 10. Of course, the openings 192 can also be circular or other shapes to accommodate the specific size. The openings 192 are aligned in a row so that each apparatus is separated from its adjacent apparatus and is housed within the opening well 19 so that the apparatus is retained in a safe and sanitary manner. After all of the apparatuses have been used, the apparatus retaining member 190 is discarded and a new apparatus retaining member with a fully loaded interchangeable removable member is inserted. While the illustration shows all of the same apparatus in each case, it is within the spirit and scope of the present invention to have several different interchangeable removable members in the same apparatus retaining member 190.

The inverted frustum shaped cavity further comprises sidewalls which are set at an angle of approximately 20 degrees relative to the longitudinal axis of the head and said arcuate cavity further comprises sidewalls which are set an angle of approximately 20 degrees relative to the longitudinal axis of the head whereby the stem of the interchangeable removable member can be moved in a 20 degree arc within the arcuate cavity and the shank of the interchangeable removable member can be moved in a 20 degree arc within the inverted frustum shaped cavity to thereby orient the dental applicator part at a desired angle relative to the head.

Figure 12:
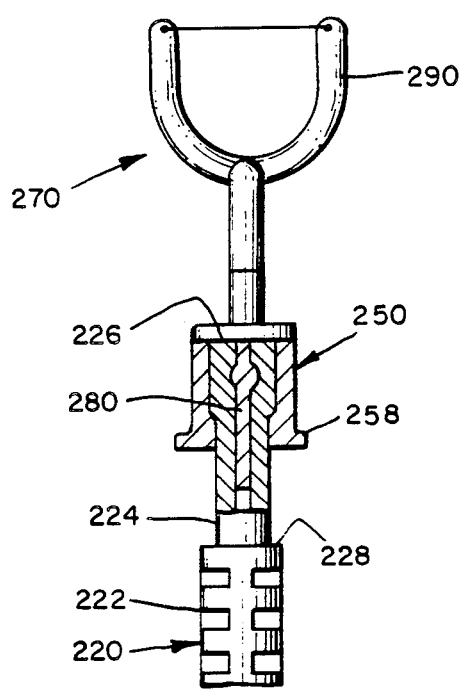
FIG. 12 is a front elevational view of an alternative embodiment of the present invention dental applicator shown in partial cross-section with an interchangeable member being a yoke supporting a length of dental floss between the arms of the yoke supported in the handle.
Figure 13:
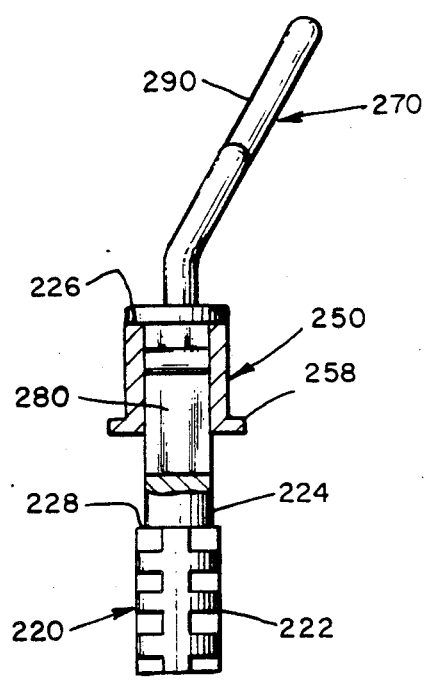
FIG. 13 is a side elevational view of the alternative embodiment of the present invention dental applicator shown in partial cross-section with an alternative embodiment of the interchangeable member being a yoke supporting a length of dental floss between the arms of the yoke supported in the handle.
Figure 14:
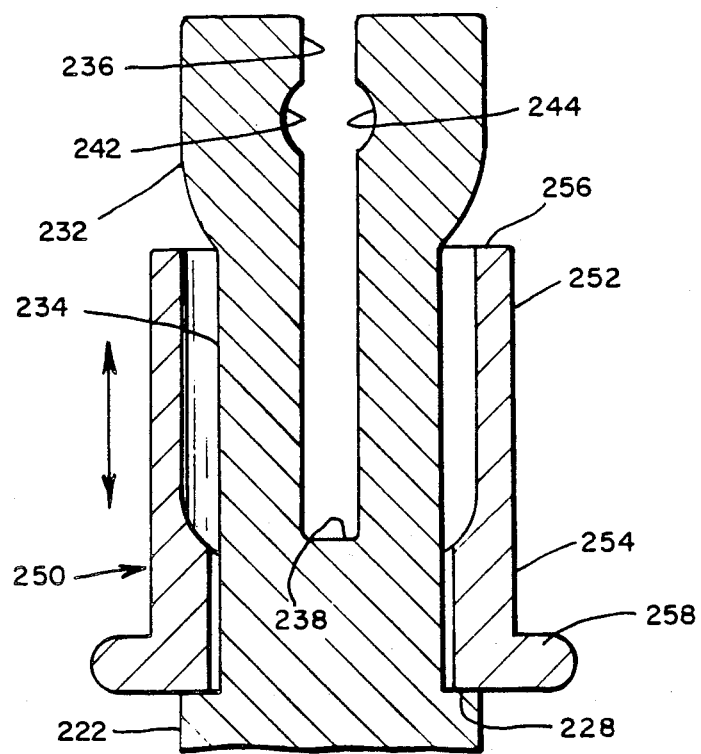
FIG. 14 is an enlarged cross-sectional view of the head and collar illustrating the specialized slit of the head of the handle.
Figure 15:
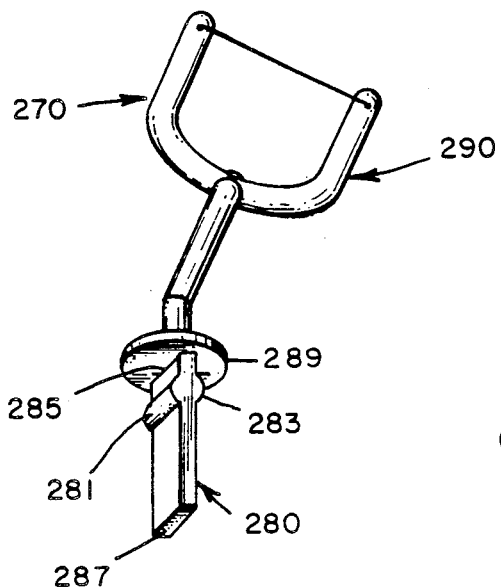
FIG. 15 is side elevational view of the alternative embodiment of the first interchangeable member which is a yoke supporting a length of dental floss between the arms of the yoke supported in the handle.
Figure 19:
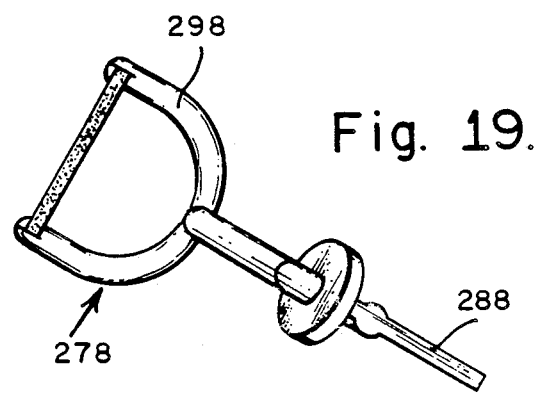
FIG. 19 is side elevational view of the alternative embodiment of the fifth interchangeable member which is a yoke supporting a length of abrasive tape between the arms of the yoke supported in the handle.
Figure 16:
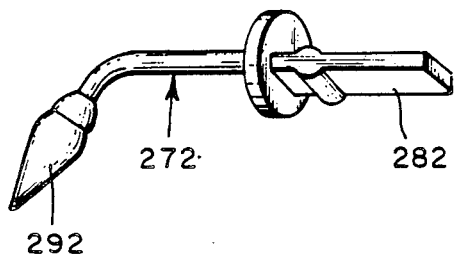
FIG. 16 is side elevational view of the alternative embodiment the second interchangeable member which is a rubber tip gum massager.
Figure 18:
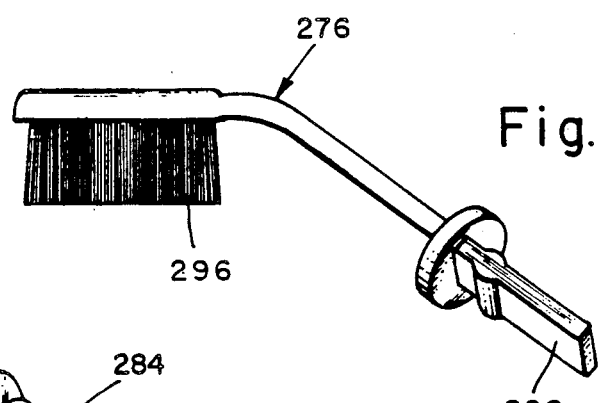
FIG. 18 is side elevational view of the alternative embodiment the fourth interchangeable member which is a toothbrush.
Figure 17:
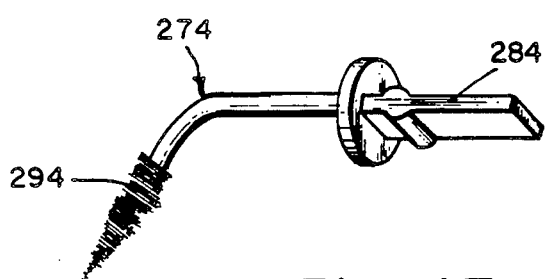
FIG. 17 is side elevational view of the alternative embodiment the third interchangeable member which is a spiral wound wire brush tooth cleaner.

Referring to FIGS. 12-19, there is shown an alternative embodiment of the present invention. FIG. 12 is a front elevational view of an alternative embodiment of the present invention dental applicator shown in partial cross-section with an interchangeable member being a yoke supporting a length of dental floss between the arms of the yoke supported in the handle; FIG. 13 is a side elevational view of the alternative embodiment of the present invention dental applicator shown in partial cross-section with an alternative embodiment of the interchangeable member being a yoke supporting a length of dental floss between the arms of the yoke supported in the handle; and FIG. 14 is an enlarged cross-sectional view of the head and collar illustrating the specialized slit of the head of the handle. Referring to FIGS. 12-14, there is shown at 220 the alternative embodiment of the specific handle of the present invention multi-purpose dental applicator. The handle 220 comprises an elongated shank section 222, a throat section 224 and a head section 226. While the shank section is shown as cylindrical, it will be appreciated that any other design such as rectangular can also be used with the present invention. While the surface of the shank is shown as smooth, it can also include ribs for more easy gripping. The cross-sectional diameter of the throat section 226 is smaller than the cross-sectional diameter of the shank section 222 to create a shoulder 228 at their conjuncture. The head section 226 has a distal portion 232 and a proximal portion 234, and a slit 236 extending from the distal portion 232 to the proximal portion 234. The proximal portion 234 is contiguous with the throat section 224 of the handle 220. The distal section 232 is widened. The bottom 238 of the slit 236 reaches into the proximal portion 234 of the head section 226. The slit 236 has two oppositely disposed inner recesses 242 and 244 which are positioned preferably within the range of the widened distal portion 232 of the head section 226. The handle further comprises a collar 250. The collar 250 also has a distal portion 252 and a proximal portion 254, and a hollow 256 extending through both the distal portion 252 and the proximal portion 254. The collar 250 has a flange 258 at the bottom of the proximal portion 254 to make it easier for a user to hold the collar 250. The hollow of the distal portion 252 of collar 250 is widened to accommodate the widened distal portion 232 of the head section 226, and the hollow of the proximal portion 254 of the collar 250 is sized to accommodate the proximal portion 234 of the head section 226 and the throat section 224. The collar 250 can be slid down from the head section 226 onto the throat section 224, where the flange 258 of the collar 250 rests on the shoulder 228 at the juncture of the shank section 222 and the throat section 224 of the handle 220. In this way, the head section 226 is loosened and can accept the stem of an associated interchangeable removable member. When the stem of an associated interchangeable removable member is inserted into the slit 236 of the head section 226, the collar can be slid up from the throat section 224 back to the head section 226. The distal portion 252 of the collar 250 is engaged to the widened distal portion 232 of the head section 226. In this way, the head section 226 is tightened and the associated interchangeable removable member is secured on the head section 226 of the handle 220.

The present invention is primarily used with five different interchangeable removable members. One such member which is the dental flossing yoke is illustrated in place in FIGS. 12 and 13, and further illustrated in detail in FIG. 15. The interchangeable removable yoke member 270 comprises two parts: a stem part 280 and a dental applicator part 290. The dental applicator part 290 is a dental flossing yoke which is similar to the dental flossing yoke previously discussed. The stem part 280 is generally rectangular shaped which has two oppositely disposed outer protrusions 281 and 283, and a distal end 285 and a proximal end 287. The dental applicator part 290 is contiguous and extends from the distal end 285 of the stem part 280, and at their juncture there is a flange 289. When the stem part 280 is inserted into the slit 236 of the head section 226 of the handle 220, the two opposite outer protrusions 281 and 283 are engaged into the two opposite inner recesses 242 and 244 respectively, and the flange 289 rests on the top of handle 220, to secure the position of the dental applicator 270. As the collar 250 is slid up, the stem 280 of the interchangeable removable member 270 is tightly clamped within the slit 236 of the head section 226 of the handle 220, to thereby fasten the interchangeable removable member 270 onto the handle 220.

Similarly, the remaining four interchangeable removable members can be inserted and used with the alternative embodiment of the handle 220. Referring to FIGS. 16-19, there are shown respectively the second interchangeable removable member 272 having a stem part 282 and a rubber tip gum massager 292; the third interchangeable removable member 274 having a stem part 284 and a spiral wound tooth cleaning brush 294; the fourth interchangeable removable member 276 having a stem part 286 and a toothbrush 296; and the fifth interchangeable removable member 278 having a stem part 288 and an abrasive tape yoke 298. All the stem parts 282, 284, 286 and 288 are incorporated with the alternative embodied stem with two opposite protrusions and a flange.

A simple case apparatus, as the ones illustrated in FIGS. 7-10 can also be used for retaining a multiplicity of a selected one of the alternatively embodied interchangeable removable members.

While the present invention has been illustrated with a dental floss yoke, a rubber tip gum massager, a spiral wound tooth cleaning brush, a toothbrush, and an abrasive tape yoke, other dental cleaning devices can also be used and employed within the spirit and scope of the present invention.

Defined in detail, the alternative embodiment of the present invention is a multi-purpose dental applicator comprising: a. a handle member further comprising (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, and (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising, (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem; and c. said dental applicator part of said interchangeable removable member further comprising (i) a yoke including a first arm having a rounded upper tip, a second arm having a rounded upper tip and a base, (ii) the first and second arms joined to the base of the yoke at their lower ends and extending away from each other to form a V-shape with the respective upper tips at the top of the V-shape, (iii) the base being integral with said distal end of said stem of said interchangeable removable member, (iv) the yoke offset at an angle relative to said stem of said interchangeable removable member, and (v) a length of dental floss bonded to the rounded tips of the yoke so that the length of dental floss is stretched taut between the tips of the yoke;

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

Defined also in detail, the alternative embodiment of the present invention is a multi-purpose dental applicator comprising:

a. a handle member further comprising (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, and (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem; and c. said dental applicator part of said interchangeable removable member further comprising (i) a yoke including a first arm having a rounded upper tip, a second arm having a rounded upper tip and a base, (ii) the first and second arms joined to the base of a yoke at their lower ends and extending away from each other to form a V-shape with the respective upper tips at the top of the V-shape, (iii) the base being integral with said distal end of said stem of said interchangeable removable member, ( the yoke offset at an angle relative to said stem of said interchangeable removable member; and (v) a length of abrasive tape affixed to the rounded tips of the yoke so that the length of abrasive tape is stretched taut between the tips of the yoke:

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

Defined again in detail, the alternative embodiment of the present invention is a multi-purpose dental applicator comprising:

a. a handle member further comprising (i) an elongated shank (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, and (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem; and c. said dental applicator part of said interchangeable removable member further comprising a shank including a rubber tip gum massager at the remote end of the shank, with the shank of said dental applicator part offset at an angle relative to said stem of said interchangeable removable member; d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

Defined again in detail, the alternative embodiment of the present invention is a multi-purpose dental applicator comprising:

a. a handle member further comprising (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, and (v) a slidable collar partially resting around the throat section of the handle, and having a distal portion and proximal portion, a hollow extending from the distal portion to the proximal portion, distal portion of the head section;

b. an interchangeable removable member further comprising (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem; and c. said dental applicator part of aid interchangeable removable member further comprises a shank having a spiral wound wire tooth cleaning brush thereon, with the shank of said dental applicator part offset at an angle relative to said stem of said interchangeable removable member;

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

Defined further in detail, the alternative embodiment of the present invention is a multi-purpose dental applicator comprising:

a. a handle member further comprising (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, and (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem; and c. said dental applicator part of said interchangeable removable member further comprises a shank having a spiral wound wire tooth cleaning brush thereon, with the shank of said dental applicator part offset at an angle relative to said stem of said interchangeable removable member;

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

In the preferred alternative embodiments of the present invention defined in detail: (a) the dental applicator part of the interchangeable removable member is offset at an angle of approximately 35 degrees relative to the stem of the interchangeable removable member; and (b) the multi-purpose dental applicator further comprises a retaining container including a shelf for supporting a removable tray having a multiplicity of retaining wells for respectively retaining the dental applicator part of an individual interchangeable removable member within an individual retaining well with the stem of each interchangeable removable member extending upwardly from the tray.

Defined broadly, the alternative embodiment of the present invention is a multi-purpose dental applicator comprising:

a. a handle member further comprising (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, and (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section; and b. an interchangeable removable member further comprising (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem;

c. whereby said interchangeable removable member can be removably retained onto said head section of said handle member by inserting said elongated stem into said elongated slit while said collar is resting partially around said throat section of said handle member, such that said two said two opposite inner recesses of said elongated slit, and said collar is then slid onto said head section of said handle member to thereby tighten said interchangeable removable member to said handle member.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus is intended only for illustration and for disclosure of an operative embodiment and not to show all of the various forms of modification in which the invention might be embodied or operated. The invention has been described in considerable detail in order to comply with the patent laws by providing full public disclosure of at least one of its forms. However, such detailed description is not intended in any way to limit the broad features or principles of the invention, or the scope of patent monopoly to be granted.

What is claimed is:

1. A multi-purpose dental applicator comprising:

a. a handle member further comprising, (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising, (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem;

c. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

2. A multi-purpose dental applicator in accordance with claim 1 wherein said dental applicator part of said interchangeable removable member further comprises:
   a. a yoke including a first arm having a rounded upper tip, a second arm having a rounded upper tip and a base;
   b. the first and second arms joined to the base of the yoke at their lower ends and extending away from each other to form a V-shape with the respective upper tips at the top of the V-shape;
   c. the base being integral with said distal end of said stem of said interchangeable removable member;
   d. the yoke offset at an angle relative to said stem of said interchangeable removable member; and
   e. a length of dental floss bonded to the rounded tips of the yoke so that the length of dental floss is stretched taut between the tips of the yoke.

3. A multi-purpose dental applicator in accordance with claim 2 wherein said yoke is offset at an angle of approximately 35 degrees relative to said stem of said interchangeable removable member.

4. A multi-purpose dental applicator in accordance with claim 2 further comprising a retaining container including a shelf for supporting a removable tray, which removable tray further comprises a multiplicity of retaining wells for respectively retaining said dental applicator part of an individual interchangeable removable member within an individual retaining well to shield said dental floss massager, with said stem of each interchangeable removable member extending upwardly from the tray.

5. A multi-purpose dental applicator in accordance with claim 1 wherein said dental applicator part of said interchangeable removable member further comprises:
   a. a yoke including a first arm having a rounded upper tip, a second arm having a rounded upper tip and a base;
   b. the first and second arms joined to the base of the yoke at their lower ends and extending away from each other to form a V-shape with the respective upper tips at the top of the V-shape;
   c. the base being integral with said distal end of said stem of said interchangeable removable member;
   d. the yoke offset at an angle relative to said stem of said interchangeable removable member; and
   e. a length of abrasive tape affixed to the rounded tips of the yoke so that the length of abrasive tape is stretched taut between the tips of the yoke.

6. A multi-purpose dental applicator in accordance with claim 5 wherein said yoke is offset at an angle of approximately 35 degrees relative to said stem of said interchangeable removable member.

7. A multi-purpose dental applicator in accordance with claim 5 further comprising a retaining container including a shelf for supporting a removable tray, which removable tray further comprises a multiplicity of retaining wells for respectively retaining said dental applicator part of an individual interchangeable removable member within an individual retaining well to shield said abrasive tape, with said stem of each interchangeable removable member extending upwardly from the tray.

8. A multi-purpose dental applicator in accordance with claim 1 wherein said dental applicator part of said interchangeable removable member further comprises a shank including a rubber tip gum massager at the remote end of the shank, with the shank of said dental applicator part offset at an angle relative to said stem of said interchangeable removable member.

9. A multi-purpose dental applicator in accordance with claim 8 further comprising a retaining container including a shelf for supporting a removable tray, which removable tray further comprises a multiplicity of retaining wells for respectively retaining said dental applicator part of an individual interchangeable removable member within an individual retaining well to shield said rubber tip massager, with said stem of each interchangeable removable member extending upwardly from the tray.

10. A multi-purpose dental applicator in accordance with claim 1 wherein said dental applicator part of said interchangeable removable member further comprises a shank having a spiral wound wire tooth cleaning brush thereon, with the shank of said dental applicator part offset at an angle relative to said stem of said interchangeable removable member.

11. A multi-purpose dental applicator in accordance with claim 10 further comprising a retaining container including a shelf for supporting a removable tray, which removable tray further comprises a multiplicity of retaining wells for respectively retaining said dental applicator part of an individual interchangeable removable member within an individual retaining well to shield said spiral wound wire tooth cleaning brush, with said stem of each interchangeable removable member extending upwardly from the tray.

12. A multi-purpose dental applicator in accordance with claim 1 wherein said dental applicator part of said interchangeable removable member further comprises a shank having a toothbrush head including bristles thereon, with the shank of said dental applicator part offset at an angle relative to said stem of said interchangeable removable member.

13. A multi-purpose dental applicator in accordance with claim 12 further comprising a retaining container including a shelf for supporting a removable tray, which removable tray further comprises a multiplicity of retaining wells for respectively retaining said dental applicator part of an individual interchangeable removable member within an individual retaining well to shield said toothbrush head including bristles, with said stem of each interchangeable removable member extending upwardly from the tray.

14. A multi-purpose dental applicator comprising:
   a. a handle member further comprising,
      (i) an elongated shank,
      (ii) a throat section extending from the elongated shank and extending to a head section,
      (iii) the head section having a distal portion and a proximal portion, and an elongated slit extending from the distal portion to the proximal portion, where the elongated slit has two oppositely disposed inner recesses,
      (iv) the distal portion of the head section being widened,
      (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;
   b. an interchangeable removable member further comprising, (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, and (iv) a dental applicator part integral with the distal end of the elongated stem;

c. said dental applicator part of said interchangeable removable member further comprising, (i) a yoke including a first arm having a rounded upper tip, a second arm having a rounded upper tip and a base, (ii) the first and second arms joined to the base of the yoke at their lower ends and extending away from each other to from a V-shape with the respective upper tips at the top of the V-shape, (iii) the base being integral with said distal end of said stem of said interchangeable removable member, (iv) the yoke offset at an angle relative to said stem of said interchangeable removable member, and (v) a length of dental floss bonded to the rounded tips of the yoke so that the length of dental floss is stretched taut between the tips of the yoke;

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

15. A multi-purpose dental applicator in accordance with claim 14 wherein said yoke is offset at an angle of approximately 35 degrees relative to said stem of said interchangeable removable member.

16. A multi-purpose dental applicator in accordance with claim 14 further comprising a retaining container including a shelf for supporting a removable tray, which removable tray further comprises a multiplicity of retaining wells for respectively retaining said dental applicator part of an individual interchangeable removable member within an individual retaining well to shield said dental floss massager, with said stem of each interchangeable removable member extending upwardly from the tray.

17. A multi-purpose dental applicator comprising:

a. a handle member further comprising, (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses, (iv) the distal portion of the head section being widened, (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising, (i) an elongated stem having a distal end and a proximal end, (ii) the elongated stem having two oppositely disposed outer protrusions for engaging into said two inner recesses of said elongated slit of said head section of said handle member, (iii) the elongated stem having a flange at its distal end, (iv) a dental applicator part integral with the distal end of the elongated stem;

c. said dental applicator part of said interchangeable removable member further comprising, (i) a yoke including a first arm having a rounded upper tip, a second arm having a rounded upper tip and a base, (ii) the first and second arms joined to the base of the yoke at their lower ends and extending away from each other to form a V-shape with the respective upper tips at the top of the V-shape, (iii) the base being integral with said distal end of said stem of said interchangeable removable member, (iv) the yoke offset at an angle relative to said stem of said interchangeable removable member; and (v) a length of abrasive tape affixed to the rounded tips of the yoke so that the length of abrasive tape is stretched taut between the tips of the yoke;

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

18. A multi-purpose dental applicator in accordance with claim 17 wherein said yoke is offset at an angle of approximately 35 degrees relative to said stem of said interchangeable removable member.

19. A multi-purpose dental applicator in accordance with claim 17 further comprising a retaining container including a shelf for supporting a removable tray, which removable tray further comprises a multiplicity of retaining wells for respectively retaining said dental applicator part of an individual interchangeable removable member within an individual retaining well to shield said abrasive tape, with said stem of each interchangeable removable member extending upwardly from the tray.

20. A multi-purpose dental applicator comprising:

a. a handle member further comprising, (i) an elongated shank, (ii) a throat section extending from the elongated shank and extending to a head section, (iii) the head section having a distal portion and a proximal portion, and an elongated slit extending from the distal portion to the proximal portion, where the elongated slit has two oppositely disposed inner recesses,
(iv) the distal portion of the head section being widened,
(v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;
b. an interchangeable removable member further comprising,
(i) an elongated stem having a distal end and a proximal end,
(ii) the elongated stem having two oppositely disposed outer protrusions for engaging into said two inner recesses of said elongated slit of said head section of said handle member,
(iii) the elongated stem having a flange at its distal end,
(iv) a dental applicator part integral with the distal end of the elongated stem; and
c. said dental applicator part of said interchangeable removable member further comprising a shank including a rubber tip gum massager at the remote end of the shank, with the shank of said dental applicator part offset at an angle relative to said stem of said interchangeable removable member;
d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

21. A multi-purpose dental applicator in accordance with claim 20 wherein said shank and said rubber tip gum massager of said dental applicator part is offset at an angle of approximately 35 degrees relative to said stem of said interchangeable removable member.

22. A multi-purpose dental applicator in accordance with claim 20 further comprising a retaining container including a shelf for supporting a removable tray, which removable tray further comprises a multiplicity of retaining wells for respectively retaining said dental applicator part of an individual interchangeable removable member within an individual retaining well to shield said rubber tip massager, with said stem of each interchangeable removable member extending upwardly from the tray.

23. A multi-purpose dental applicator comprising:
a. a handle member further comprising,
(i) an elongated shank,
(ii) a throat section extending from the elongated shank and extending to a head section,
(iii) the head section having a distal portion and a proximal portion, and an elongated slit extending from the distal portion to the proximal portion, where the elongated slit has two oppositely disposed inner recesses,
(iv) the distal portion of the head section being widened,
(v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;
b. an interchangeable removable member further comprising,
(i) an elongated stem having a distal end and a proximal end,
(ii) the elongated stem having two oppositely disposed outer protrusions for engaging into said two inner recesses of said elongated slit of said head section of said handle member,
(iii) the elongated stem having a flange at its distal end,
(iv) a dental applicator part integral with the distal end of the elongated stem; and
c. said dental applicator part of said interchangeable removable member further comprises a shank having a spiral wound wire tooth cleaning brush thereon, with the shank of said dental applicator part offset at an angle relative to said stem of said interchangeable removable member;
d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

24. A multi-purpose dental applicator in accordance with claim 23 wherein said shank and said spiral wound wire tooth cleaning brush of said dental applicator part is offset at an angle of approximately 35 degrees relative to said stem of said interchangeable removable member.

25. A multi-purpose dental applicator in accordance with claim 23 further comprising a retaining container including a shelf for supporting a removable tray, which removable tray further comprises a multiplicity of retaining wells for respectively retaining said dental applicator part of an individual interchangeable removable member within an individual retaining well to shield said spiral wound wire tooth cleaning brush, with said stem of each interchangeable removable member extending upwardly from the tray.

26. A multi-purpose dental applicator comprising:
a. a handle member further comprising,
(i) an elongated shank,
(ii) a throat section extending from the elongated shank and extending to a head section,
(iii) the head section having a distal portion and a proximal portion, and an elongated slit extending from the distal portion to the proximal portion, where the elongated slit has two oppositely disposed inner recesses,
(iv) the distal portion of the head section being widened, (v) a slidable collar partially resting around the throat section of the handle, and having a distal portion and proximal portion, a hollow extending from the distal portion to the proximal portion, and a flange at its proximal portion, where the hollow of the distal portion is widened to accommodate the widened distal portion of the head section;

b. an interchangeable removable member further comprising,
  (i) an elongated stem having a distal end and a proximal end,
  (ii) the elongated stem having two oppositely disposed outer protrusions for engaging into said two inner recesses of said elongated slit of said head section of said handle member,
  (iii) the elongated stem having a flange at its distal end,
  (iv) a dental applicator part integral with the distal end of the elongated stem; and c. said dental applicator part of said interchangeable removable member further comprises a shank having a toothbrush head including bristles thereon, with the shank of said dental applicator part offset at an angle relative to said stem of said interchangeable removable member;

d. whereby said interchangeable removable member can be removably retained onto said head section of said handle member by inserting said elongated stem into said elongated slit while said collar is resting partially around said throat section of said handle member, such that said two opposite outer protrusions of said stem are engaged into said two opposite inner recesses of said elongated slit, and said collar is then slid onto said head section of said handle member to thereby tighten said interchangeable removable member to said handle member.

27. A multi-purpose dental applicator in accordance with claim 26 wherein said shank and said toothbrush head including bristles of said dental applicator part is offset at an angle of approximately 35 degrees relative to said stem of said interchangeable removable member.

28. A multi-purpose dental applicator in accordance with claim 26 further comprising a retaining container including a shelf for supporting a removable tray, which removable tray further comprises a multiplicity of retaining wells for respectively retaining said dental applicator part of an individual interchangeable removable member within an individual retaining well to shield said toothbrush head including bristles, with said stem of each interchangeable removable member extending upwardly from the tray.

* * * * *